United States Patent [19]

Vermehren et al.

[11] Patent Number: 5,164,393
[45] Date of Patent: Nov. 17, 1992

[54] PYRIMIDINE DERIVATIVES COMPOSITIONS CONTAINING THEM, AND THEIR USE AS FUNGICIDES

[75] Inventors: Jan Vermehren; Wolfgang Giencke, both of Hofheim am Taunus; Peter Braun, Mainz; Burkhard Sachse, Kelkheim, all of Fed. Rep. of Germany

[73] Assignee: Hoechst Aktiengesellschaft, Frankfurt am Main, Fed. Rep. of Germany

[21] Appl. No.: 776,811

[22] Filed: Oct. 15, 1991

[30] Foreign Application Priority Data

Oct. 17, 1990 [DE] Fed. Rep. of Germany ....... 4032878

[51] Int. Cl.$^5$ ................. C07D 239/70; C07D 239/72; C07D 401/04; A01N 43/54
[52] U.S. Cl. .................... 514/256; 514/259; 514/258; 514/269; 544/333; 544/319; 544/298; 544/283; 544/287; 544/253; 544/284
[58] Field of Search ............. 544/333, 319, 298, 283, 544/287, 253, 284; 514/259, 256

[56] References Cited

FOREIGN PATENT DOCUMENTS 270362 6/1988 European Pat. Off. .

Primary Examiner—John M. Ford
Attorney, Agent, or Firm—Curtis, Morris & Safford

[57] ABSTRACT

Pyrimidine derivatives of the formula I

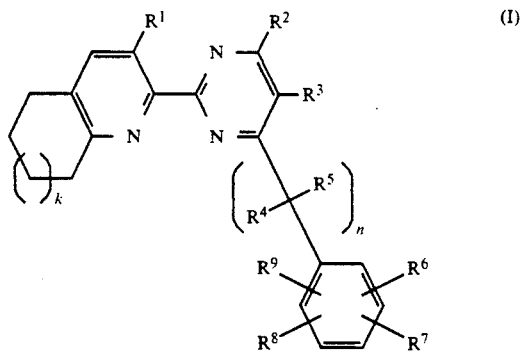

in which the variables are herein below described in the specification.

$R^3$, $R^4$ and $R^5$ optionally together with the radical $R^3$ are a component of a maximally unsaturated $\lambda$-membered ring where $\lambda$ is 3 to 8, two radicals $R^6$ to $R^9$ together may form a component of an unsaturated or saturated m-membered ring where m is 5 or 6, k is 0, 1 or 2, n is 1 or 2 and the addition salts thereof, their preparation, compositions containing them, and their use in the control of harmful fungi.

4 Claims, No Drawings

PYRIMIDINE DERIVATIVES COMPOSITIONS CONTAINING THEM, AND THEIR USE AS FUNGICIDES

The present invention relates to pyrimidine derivatives, to their preparation, to compositions containing them, and to their use as fungicides.

It has already been disclosed that pyrimidine derivatives are effective components in fungicidal compositions (cf. EP-A-270,362, EP-A-259,139, EP-A-234,104). However, the action of these pyrimidine derivatives is not always satisfactory, in particular when low application rates are used.

Novel pyrimidine derivatives have been found, and these have advantageous effects on the control of a broad range of phytopathogenic fungi, in particular when low dosage rates are used.

The present invention therefore relates to compounds of the formula I

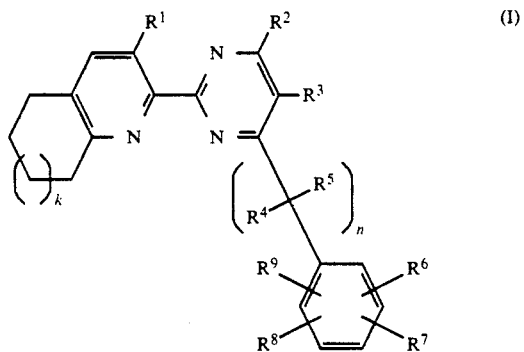

in which
$R^1$ is hydrogen, $(C_1-C_6)$alkyl, $(C_1-C_6)$alkoxy, phenyl-$(C_1-C_4)$alkyl, it being possible for the phenyl moiety to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, $R^2$ is hydrogen, hydroxyl, $(C_2-C_4)$alkenyl-$(C_1-C_4)$alkyl, $(C_2-C_4)$alkynyl-$(C_1-C_4)$alkyl, $(C_1-C_6)$alkyl, $(C_1-C_6)$alkoxy-$(C_1-C_4$alkyl, $(C_2-C_6)$alkenyl, $(C_2-C_6)$alkynyl, $(C_3-C_7)$cycloalkyl, $(C_3-C_7)$cycloalkyl-$(C_1-C_4)$alkyl, it being possible for the two last-mentioned radicals to be up to trisubstituted in the cycloalkyl moiety by $(C_1-C_4)$alkyl, or is phenyl, phenoxy-$(C_1-C_4)$alkyl, phenyl-$(C_1-C_4)$alkyl, it being possible for the three last-mentioned radicals to be up to trisubstituted in the phenyl moiety by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, or is $(C_1-C_{12}$alkoxy, $(C_2-C_6)$alkenyl-$(C_1-C_4)$alkoxy, $(C_2-C_6)$alkynyl-$(C_1-C_4)$alkoxy, $(C_3-C_7)$cycloalkoxy, $(C_1-C_6)$alkoxy-$(C_1-C_6)$alkoxy, hydroxy-$(C_1-C_6)$alkoxy, $(C_1-C_6)$haloalkoxy, $(C_1-C_6)$-alkylthio, $(C_2-C_6)$alkenyl-$(C_1-C_4)$alkylthio, $(C_2-C_6)$-alkynyl-$(C_1-C_4)$alkylthio, $(C_3-C_7)$cycloalkylthio, phenoxy, phenylthio, phenyl-$(C_1-C_5)$alkoxy, phenyl-$(C_1-C_6)$alkylthio, phenyl-$(C_1-C_2)$alkoxy-$(C_1-C_4)$alkoxy, it being possible for the phenyl ring in the five last-mentioned radicals to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy or mono-substituted by nitro or cyano, $R^3$ is hydrogen, $(C_1-C_5)$alkyl, $(C_1-C_4)$haloalkyl, $(C_1-C_4)$alkoxy, $(C_1-C_4)$alkylthio, halogen, phenyl, phenyl-$(C_1-C_4)$alkyl, it being possible for the phenyl radical of the three last-mentioned radicals to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy or monosubstituted by nitro or cyano, $R^4$ and $R^5$ independently of one another are hydrogen $(C_1-C_6)$alkyl, or $R^3$ together with $R^4$ or $R^5$ is a component of a maximally unsaturated $\gamma$-membered ring where $\gamma = 3$ to 8, $R^6$, $R^7$, $R^8$ and $R^9$ independently of one another are hydrogen, halogen, nitro, cyano, $(C_1-C_6)$alkyl, $(C_1-C_6)$alkoxy, $(C_1-C_6)$alkylthio, $(C_1-C_6)$haloalkyl, $(C_1-C_6)$haloalkoxy, aryl, aryloxy, it being possible for the two last-mentioned radicals to be up to trisubstituted in the aryl radical by halogen, $(C_1-C_4)$alkyl, $(C_1-C_4)$alkoxy, $(C_1-C_4)$haloalkyl or $(C_1-C_4)$haloalkoxy, two of the radicals $R^6$ to $R^9$ may form a component of an unsaturated or saturated m-membered ring where m is 5 or 6, k is 0, 1 or 2, n is 1 or 2 and halo has the meaning of monosubstituted or polysubstituted by halogen atoms, and the acid addition salts thereof.

Preferred compounds amongst those of the formula I are those in which $R^1$ is hydrogen, $(C_1-C_4)$alkyl, $(C_1-C_6)$alkoxy, $R^2$ is hydrogen, hydroxyl, $(C_1-C_4)$alkyl, $(C_2-C_4)$alkenyl$(C_1-C_2)$alkyl, $(C_2-C_4)$alkynyl-$(C_1-C_2)$alkyl, $(C_1-C_4)$alkoxy-$(C_1-C_4)$alkyl, $(C_2-C_4)$alkenyl, $(C_2-C_4)$alkynyl, $(C_3-C_6)$cycloalkyl, $(C_3-C_6)$cycloalkyl-$(C_1-C_2)$alkyl, it being possible for the two last-mentioned radicals to be up to trisubstituted in the cycloalkyl moiety by $(C_1-C_4)$alkyl, or is phenyl, phenoxy-$(C_1-C_2)$alkyl, phenyl$(C_1-C_2)$alkyl, it being possible for the three last-mentioned radicals to be up to trisubstituted in the phenyl moiety by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, or is $(C_1-C_{12})$alkoxy, $(C_2-C_4)$alkenyl-$(C_1-C_2)$alkoxy, $(C_2-C_4)$alkynyl-$(C_1-C_2)$alkoxy, $(C_3-C_6)$cycloalkyloxy, $(C_1-C_4)$alkoxy-$(C_1-C_4)$alkoxy, hydroxy-$(C_1-C_4)$alkoxy, $(C_1-C_6)$haloalkoxy, $(C_1-C_6)$alkylthio, $(C_2-C_6)$alkenyl-$(C_1-C_2)$alkylthio, $(C_2-C_4)$-alkenyl-$(C_1-C_2$alkylthio, $(C_3-C_6)$cycloalkylthio, phenoxy, phenylthio, phenyl-$(C_1-C_2)$alkoxy, phenyl)$C_1-C_2)$alkylthio, phenyl-$(C_1-C_2)$alkoxy-$(C_1-C_4)$alkoxy, it being possible for the phenyl ring in the four last-mentioned radicals to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, $R^3$ is hydrogen, $(C_1-C_4)$alkyl, $(C_1-C_4)$haloalkyl, $(C_1-C_4)$alkoxy, $(C_1-C_4)$alkylthio, halogen, phenyl, phenyl$(C_1-C_2)$alkyl, $R^4$ and $R^5$ independently of one another are hydrogen or $(C_1-C_2)$alkyl or $R^3$ together with $R^4$ or $R^5$ is a component of a maximally unsaturated $\gamma$-membered ring where $\gamma$ is 5 or 6, $R^6$, $R^7$, $R^8$ and $R^9$ independently of one another are hydrogen, halogen, nitro, cyano, $(C_1-C_4)$alkyl, $(C_1-C_4)$alkoxy, $(C_1-C_4)$haloalkyl, $(C_1-C_4)$haloalkoxy, phenyl, phenyloxy, it being possible for the two last-mentioned radicals to be up to trisubstituted in the phenyl radical by halogen, $(C_1-C_4)$alkyl, $(C_1-C_4)$alkoxy, $(C_1-C_4)$haloalkyl or $(C_1-C_4)$haloalkoxy, two of the radicals $R^6$ to $R^9$ may form a component of an unsaturated or saturated m-membered ring where m is 5 or 6, k is 0, 1 or 2, n is 1 or 2 and halo has the meaning of monosubstituted or polysubstituted by halogen atoms, and the acid addition salts thereof.

In this context, the alkyl, alkenyl or alkynyl radicals can be either straight-chain or branched. Halogen denotes F, Cl, Br or I, preferably F, Cl or Br. The prefix "halo" in the designation of a substituent, here and hereinafter, means that the substituent can occur once or more than once having an identical or different meaning. The prefix "halo" embraces fluorine, chlorine, bromine or iodine, in particular fluorine, chlorine or bromine. The following may be mentioned as examples of haloalkanes: $CF_3$, $CF_2CHF_2$, $CCl_3$, $CCl_2F$, $CF_2CF_2CF_3$, $CF_2CHFCF_3$, $CH_2CF_3$ and $(CF_2)_3CF_3$.

The following acids are suitable for preparing the acid addition salts of the compounds of the formula I:

Hydrohalic acids such as hydrochloric acid or hydrobromic acid, furthermore phosphoric acid, nitric acid, sulfuric acid, mono- or bifunctional carboxylic acids and hydroxycarboxylic acids such as acetic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition salts of the compounds of the formula I can be obtained in a simple manner by customary salt formation methods, for example by dissolving them in an organic solvent and adding the acid, and they can be isolated in a known manner, for example by filtration, and, if appropriate, purified by washing with an inert solvent.

The present invention also relates to a process for the preparation of the compounds of the formula I. The novel pyrimidine derivatives of the formula I can be prepared by the following method:

a) Pyrimidine derivatives of the formula I in which $R^2$ is H are obtained following the equation below, by reductive dehalogenation of corresponding halopyrimidines of the formula I in which $R^2$ is halogen (Cl, Br, I) and the remaining substituents are as defined in formula I. The dehalogenation can be carried out using hydrogen in the presence of catalysts (for example palladium/charcoal) in an inert solvent, for example water, lower alcohol (such as methanol or ethanol), ethyl acetate or toluene, or mixtures of these. It is advantageous to add bases such as hydroxides or carbonates of alkali metals or alkaline earth metals. The reaction is preferably carried out in the range from 15°-60° C. and under a hydrogen pressure from 1 to 5 bar.

b) Pyrimidine derivatives of the formula I in which $R^2$ is $(C_1-C_{12})$alkoxy, $(C_1-C_6)$alkylthio, $(C_2-C_6)$alkenyl-$(C_1-C_4)$alkoxy, $(C_2-C_6)$alkenyl-$(C_1-C_4)$alkylthio, $(C_2-C_6)$alkynyl$(C_1-C_4)$alkoxy, $(C_2-C_6)$alkynyl-$(C_1-C_4)$alkylthio, $(C_3-C_7)$cycloalkyloxy, $(C_3-C_7)$cycloalkylthio, hydroxy-$(C_1-C_4)$alkoxy, $(C_1-C_4)$haloalkoxy, $(C_1-C_4)$alkoxy-$(C_1-C_4)$alkoxy, phenoxy, phenylthio, phenyl-$(C_1-C_6)$alkoxy, phenyl-$(C_1-C_6)$alkylthio, phenyl-$(C_1-C_2)$alkoxy-$(C_1-C_4)$alkoxy, it being possible for the five last-mentioned radicals to be unsubstituted or up to trisubstituted in the phenyl moiety by halogen, $(C_1-C_4)$alkyl, $(C_1-C_4)$alkoxy, $(C_1-C_2)$haloalkoxy or $(C_1-C_3)$haloalkoxy, are obtained by reacting corresponding halopyrimidines of the formula I ($R^2$=halogen) with an alkali metal compound of the formula $R^2$—Y (II) in which $R^2$ is as defined above and Y is an alkali metal. Examples of alkali metals are sodium, potassium and lithium. The reaction is carried out between 0° C. and 130° C. in the course of 0.5 to 72 hours. The alkali metal compound $R^2$—Y is employed in amounts of from 1 to 2 mol equivalents based on 1 equivalent of the halopyrimidine (I)

($R^2$=halogen). The reaction is carried out in the presence of a solvent.

If an alkali metal compound $R^2$—Y of the formula II is employed in which $R^2$ is $(C_1-C_{12})$alkoxy, $(C_2-C_6)$alkenyl$(C_1-C_4)$alkoxy, $(C_2-C_6)$alkynyl-$(C_1-C_4)$alkoxy, $(C_1-C_4)$haloalkoxy, $(C_1-C_4)$alkoxy-$(C_1-C_4)$alkoxy, phenyl-$(C_1-C_2)$alkoxy$(C_1-C_4)$alkoxy or phenyl-$(C_1-C_2)$alkoxy, it is advantageous to use the corresponding alcohol $R^2$—H or an ether (for example diethyl ether, dioxane or tetrahydrofuran) or a mixture of these as the solvent. In those cases in which an alkali metal compound $R^2$—Y is used in which $R^2$ is $(C_1-C_6)$alkylthio, $(C_1-C_4)$alkylthio-$(C_1-C_4)$alkylthio, phenoxy, phenylthio or phenyl-$(C_1-C_2)$-alkylthio, an ether (for example diethyl ether, dioxane or tetrahydrofuran), a nitrile (for example acetonitrile), an aromatic hydrocarbon (for example toluene or xylene) or a mixture of these is used as the solvent.

c) Pyrimidine derivatives of the formula I in which $R^2$ is $(C_1-C_6)$alkyl, $(C_1-C_4)$alkoxy-$(C_1-C_4)$alkyl, $(C_2-C_6)$alkenyl, $(C_2-C_6)$alkynyl, $(C_3-C_7)$cycloalkyl, $(C_3-C_7)$cycloalkyl$(C_1-C_4)$alkyl, it being possible for the two last-mentioned radicals to be up to trisubstituted in the cycloalkyl moiety by $(C_1-C_4)$alkyl, or is phenyl, phenoxy-$(C_1-C_4)$alkyl, phenyl-$(C_1-C_4)$alkyl, it being possible for the three last-mentioned radicals to be up to trisubstituted in the phenyl moiety by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, are obtained by reacting corresponding halopyrimidines I ($R^2$=halogen) with Grignard compounds $R^2$—MgX (III) where $R^2$ is as defined above and X is halogen (Cl, Br, I), in the presence of a catalyst, for example 1,2-bis-(diphenylphosphino)ethane nickel(II) chloride or 1,2-bis(diphenylphosphino)propane nickel(II) chloride (cf. Chem. Pharm. Bull. Vol. 26, 2160 (1978) and Pure & Appl. Chem. Vol. 52, 669 (1980)). The reaction is carried out between 0° C. and 80° C. or at the boiling point of the solvent. The Grignard compound $R^2$—MgX of the formula III is employed in amounts of from 1 to 2.5 mol equivalents based on 1 equivalent of halopyrimidine (I). Suitable solvents are ethers such as diethyl ether, dioxane, tetrahydrofuran or dimethoxyethane.

The halopyrimidines of the formula I can be obtained by reacting the corresponding hydroxypyrimidines I ($R^2$=OH) in which the radicals $R^1$ and $R^3$ to $R^9$ are as defined in the formula I, with halogenating reagents. Halogenating reagents which can be employed are, for example, thionyl chloride, phosgene, phosphorus oxychloride, phosphorus pentachloride, phosphorus oxybromide or phosphorus tribromide. The reactions can be carried out in a solvent but also in the absence of a solvent. The halogenating reagent is employed in amounts of 1 to 4 equivalents based on 1 equivalent of the hydroxypyrimidine I ($R^2$=OH).

The reactions are carried out in a temperature range of from 25°-160° C. Preferred solvents which are employed are aromatic hydrocarbons (for example benzene or toluene, inter alia) or halogenated hydrocarbons (for example chlorobenzene, dichloromethane or 1,2-dichloroethane).

The hydroxypyrimidines of the formula I where $R^2$ is OH are novel and can be prepared by processes known from the literature (cf. G. W. Miller, F. L. Rose, J. Soc. Chem. 1963, 5643).

The compounds of the formula I according to the invention are distinguished by an outstanding fungicidal action. Fungal pathogens which have already penetrated the plant tissue can be successfully controlled in a curative manner. This is particularly important and advantageous in the case of those fungal diseases which can no longer be effectively controlled by the usual fungicides once infection has taken place. The spectrum of action of the claimed compounds embraces a large number of various economically important phytopathogenic fungi, for example Piricularia oryzae, Leptosphaeria nodorum, Pyrenophora teres, powdery mildews, various rusts and Botrytis cinerea, and also the fungi Plasmopara viticola and Phytophthora infestans from the Oomycetes.

Moreover, the compounds according to the invention are also suitable for use in technical fields, for example as wood preservatives, as preservatives in paints, in cooling lubricants for metal working, or as preservatives in drilling and cutting oils.

The invention also relates to compositions which contain the compounds of the formula I, besides suitable formulation auxiliaries. The compositions according to the invention generally contain the active substances of the formula I in amounts from 1 to 95% by weight.

They can be formulated in various ways, depending on the biological and/or chemico-physical parameters. The following are therefore suitable possibilities of formulation: wettable powders (WP), emulsifiable concentrates (EC), aqueous dispersions on an oil or water base (SC), suspoemulsions (SC), dusts (DP), seed-treatment agents, granules in the form of water-dispersible granules (WG), ULV formulations, microcapsules, waxes or baits.

These individual types of formulation are known in principle and are described, for example, in: Winnacker-Kuchler, "Chemische Technologie" [Chemical Technology], Volume 7, C. Hauser Verlag Munich, 4th Edition 1986; van Falkenberg, "Pesticides Formulations", Marcel Dekker N.Y., 2nd Ed. 1972-73; K. Martens, "Spray Drying Handbook", 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Book, Caldwell N.J.; H. v. Olphen, "Introduction to Clay Colloid Chemistry", 2nd. Ed., J. Wiley & Sons, N.Y.; Marschen, "Solvents Guide", 2nd Ed., Interscience, N.Y. 1950; McCutcheon's "Detergents and Emulsifiers Annual", Publ. Corp. Ridgewood, N.J., Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Kuchler, "Chemische Technologie" [Chemical Technology], Volume 7, C. Hauser Verlag Munich, 4th Edition 1986.

Based on these formulations, it is of course possible to prepare combinations with other pesticidally active substances, fertilizers and/or growth regulators, for example in the form of a readymix or a tank mix.

Wettable powders are preparations which are uniformly dispersible in water and which, besides the active substance, also contain wetting agents, for example, polyoxyethylated alkylphenols, polyoxyethylated fatty alcohols, alkylsulfonates or alkylphenolsulfonates, and dispersing agents, for example sodium lignosulfonate, sodium 2,2'-dinaphthylmethane-6,6'-disulfonate, sodium dibutylnaphthalenesulfonate and also sodium oleylmethyltaurinate, in addition, to a diluent or inert substance. Emulsifiable concentrates are prepared, for example, by dissolving the active substance in an inert organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as Ca dodecylbenzenesulfonate or non-ionic emulsifiers, such as fatty acid polyglycol esters, alkylaryl polyglycol ethers, fatty alcohol polyglycol ethers, propylene oxide/ethylene oxide sorbitan fatty acid esters, polyoxyethylene sorbitan fatty acid esters o polyoxyethylene sorbitol esters.

Dusts are obtained by grinding the active substance with finely divided solid substances, for example talc or natural clays, such as kaolin, bentonite or pyrophyllite, or diatomaceous earth. Granules can be produced either by spraying the active substance onto adsorptive, granulated inert material, or by applying active substance concentrates onto the surface of carriers such as sand, kaolinites or of granulated inert material, by means of adhesives, for example polyvinyl alcohol, sodium polyacrylate or alternatively mineral oils. Suitable active substances can also be granulated in the manner which is conventional for the production of fertilizer granules, if desired in a mixture with fertilizers.

The active substance concentration in wettable powders is, for example, about 10 to 90% by weight; the remainder to 100% by weight is composed of conventional formulation components. In the case of emulsifiable concentrates, the active substance concentration can be about 5 to 80% by weight. Formulations in the form of dusts usually contain 5 to 20% by weight. In the case of granules, the active substance content depends to some extent on whether the active compound is liquid or solid, which compound is present in the liquid or solid form, and on which granulation auxiliaries, fillers etc., are used.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a conventional manner, for example using water in the case of wettable powders, emulsifiable concentrates, dispersions and, in some cases, also in the case of microgranules. Preparations in the form of dusts and granules and also sprayable solutions are usually not further diluted with other inert substances before use.

The application rate required varies with the external conditions, such as temperature, humidity and the like. It can vary within wide limits. It is between 0.005 and 10.0 kg/ha of active substance; preferably, however, it is between 0.01 and 5 kg/ha of active substance.

The active substances according to the invention can be used in their commercially available formulations either on their own or in combination with other fungicides known from the literature.

Fungicides known from the literature which can be combined according to the invention with the compounds of the formula I are, for example, the following products:

Imazalil, prochloraz, fenapanil, SSF 105, triflumizol, PP 969 flutriafol, BAY-MEB 6401, propiconazol, etaconazol, tebuconazol, diclobutrazol, bitertanol, triadimefon, triadimenol, fluotrimazol, dimethomorph, tridemorph, dodemorph, fenpropimorph, falimorph, S-32165, chlobenzthiazone, parinol, buthiobat, fenpropidin, triforine, fenarimol, nuarimol, triarimol, ethirimol, dimethirimol, bupirimate, rabenzazole, triclazole, fluobenzimine, pyroxyfur, NK-483, PP-389, pyroquilon hymexazole, fenitropan, UHF-8227, cymoxanil, dichlofunanid, captafol, captan, folpet, tolyfluanid, chlorothalonil, etridiazol, iprodione, procymidon, vinclozol, metomeclan, myclozolin, dichlozolinate, fluorimide, drazoxoloan, chinomethionate, nitrothalisopropyl, dithianon, dinocap, binapacryl, fentin acetate, fentin hydroxide, carboxin, oxycarboxin, pyracarolid, methfuroxam, fenfura, furmecyclos, benodanil, mebenil, mepronil, flutalanil, fuberidazole, thiabendazole, carbendazim, benomyl, flusilazole, metalaxyl, pyrifenox, furalaxyl, methasulfocarb, probenazole, oxadixyl, diniconazole, cyprofuran, fenpiclonil, hexaconazole, difluoconazole, iprobenfos, edifenfos, diethofencarb, thiofanate thiofanatemethyl, CGD-95340 F, IKF-1216, mancozeb, maneb, zineb, nabam, thiram, probineb, prothiocarb, propamocarb, dodine, guazatine, dicloran, quintozene, chloroneb, tecnazene, biphenyl, anilazine, 2-phenylphenol, copper compounds such as Cu oxychloride, Cu oxine, Cu oxides, sulfur, fosethylaluminum, sodium dodecylbenzenesulfonate, sodium dodecyl sulfate, sodium C13/C15-alcohol ether sulfonate, sodium cetostearyl phosphate ester, dioctyl sodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyridinium bromide, ethoxylated quaternized fatty amines, alkyldimethylbenzylammonium chloride and 1-hydroxyethyl-2-alkylimidazoline.

The abovementioned components are known active substances, most of which are described in CH. R. Worthing, U. S. B. Walker and The Pesticide Manual, 7th Edition (1983), British Crop Protection Council.

Moreover, the active substances according to the invention in their commercially available formulations and in the use forms prepared from these formulations can exist as a mixture with other active substances such as insecticides, attractants, sterilants, acaricides, nematicides, fungicides, growth-regulating substances or herbicides. The insecticides include, for example, phosphoric esters, carbamates, carboxylic esters, formamidines, tin compounds, substances produced by microorganisms, and others.

The following are preferred components for mixtures:

1. from the group of the phosphoric esters azinphosethyl,azinphos-methyl,1-(4-chlorophenyl)-4-(O-ethyl,S-propyl)phosphoryloxypyrazole (TIA 230), chlorpyrifos, coumaphos, demeton, demeton-S-methyl, diazinon, dichlorvos, dimethoate, ethoprophos, etrimfos, fenitrothion, fenthion, heptenophos, parathion, parathionmethyl, phosalone, pirimiphos-ethyl, pirimiphosmethyl, profenofos, prothiofos, sulprofos, triazophos and trichlorphon.

2. from the group of the carbamates aldicarb, bendiocarb, BPMC (2-(1-methylpropyl)phenyl methylcarbamate), butocarboxim, butoxicarboxim, carbaryl, carbofuran, carbosulfan, cloethocarb, isoprocarb, methomyl, oxamyl, pyrimicarb, promecarb, propoxur and thiodicarb.

3. from the group of the carboxylic esters allethrin, alphamethrin, bioallethrin, bioresmethrin, cycloprothrin, cyfluthrin, cyhalothrin, cypermethrin, deltamethrin, alpha-cyano-3-phenyl-2-methylbenzyl 2,2-dimethyl-3-(2-chloro-2-trifluoromethylvinyl)-cyclopropanecarboxylate (FMC 54800), fenpropathrin, fenfluthrin, fenvalerate, flucythrinate, flumethrin, fluvalinate, permethrin, resmethrin, tralomethrin.

4. from the group of the formamidines amitraz and chlordimeform 5. from the group of the tin compounds azocyclotin, cyhexatin and fenbutatin oxide 6. others abamectin, Bacillus thuringiensis, bensultap, binapacryl, bromopropylate, buprofecin, camphechlor, cartap, chlorobenzilate, chlorfluazuron, 2-(4-chlorophenyl)-4,5-diphenylthiophene (UBI-T 930), chlofentezine, 2-naphthylmethyl cyclopropanecarboxylate (Ro 12-0470), cyromacin, DDT, dicofol, N-(3,5-dichloro-4-(1,1,2,2-tetrafluoroethoxy)phenylamino)carbonyl)- 2,6-difluorobenzamide (XRD 473),diflubenzuron,N-(2,3-dihydro-3-methyl-1,3-thiazol-2-ylidene)- 2,4-xylidine, dinobuton, dinocap, endosulfan, fenoxycarb, fenthiocarb, flubenzimine, flufenoxuron, gamma-HCH, hexythiazox, hydramethylnon (AC 217 300), ivermectin, 2-nitromethyl-4,5-dihydro-6H-thiazine (SD 52618), 2-nitromethyl-3,4-dihydrothiazole (SD 35651), 2-nitromethylene-1,3-thiazinan-3-ylcarbamaldehyde (WL 108 477), propargite, teflubenzuron, tetradifon, tetrasul, thiocyclam, triflumaron, and nuclear polyhedrosis and granulosis viruses.

The active substance content of the use forms prepared from the commercially available formulations can vary within wide limits, the active substance concentration of the use forms can be from 0.0001 up to 100% by weight of active substance, preferably of 0.001 to 1% by weight. They are used in one of the customary manners adapted to suit the use forms.

The following examples are intended to illustrate the invention.

A. Formulation examples a) A dust is obtained by mixing 10 parts by weight of active substance and 90 parts by weight of talc as inert substance, and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium lignosulfonate and 1 part by weight of sodium oleylmethyltaurinate as wetting and dispersing agent, and grinding the mixture in a pinned-disk mill.

c) A dispersion concentrate which is readily dispersible in water is obtained by mixing 40 parts by weight of active substance with 7 parts by weight of a sulfosuccinic monoester, 2 parts by weight of a sodium lignosulfonate and 51 parts by weight of water, and grinding the mixture in a ball mill to a fineness of below 5 microns.

d) An emulsifiable concentrate can be prepared from 15 parts by weight of active substance, 75 parts by weight of cyclohexane as the solvent, and 10 parts by weight of oxethylated nonylphenol (10 EO) as the emulsifier.

e) Granules can be prepared from 2 to 15 parts by weight of active substance and an inert granule carrier material such as attapulgite, pumice granules and/or quartz sand. It is expedient to use a suspension of the wettable powder from Example b) with a solids content of 30% and to spray this suspension onto the surface of attapulgite granules, and drying and mixing them intimately. The ratio by weight of the wettable powder is approx. 5% and that of the inert carrier material approx. 95% of the finished granules.

B. CHEMICAL EXAMPLES

EXAMPLE 1

4-(Methylnaphth-2-yl)-2-(5,6,7,8-tetrahydroquinolin-2-yl)-pyrimidine 50 mg of palladium on charcoal (5%) were added to a suspension of 2.0 g (0.0052 mol) of 4-chloro-6-(methylnapth-2-yl)-2-(5,6,7,8-tetrahydroquinolin-2-yl)-pyrimidine and 0.64 g (0.006 mol) of sodium carbonate in 150 ml of absolute methanol, under argon. The mixture was stirred vigorously for 16 hours at 25° C. under a hydrogen atmosphere. The solid was filtered off, the filtrate was concentrated, and the residue was subjected to flash chromatography (silica gel/ethyl acetate). 1.3 g (71%) of a white solid of melting point 156° C. to 158° C. are obtained.

EXAMPLE 2

6-(2,4-Dichlorobenzyl)-4-ethoxy-2-(5,6,7,8-tetrahydroquinolin-2-yl)-pyrimidine 1.95 g (0.006 mol) of a 21% strength solution of sodium ethylate in ethanol were added dropwise to the solution of 2.0 g (0.005 mol) of 4-chloro-6-(2,4-dichlorobenzyl)-2-(5,6,7,8-tetrahydroquinolin-2-yl)-pyrimidine in 50 ml of absolute ethanol. The mixture was stirred for 16 hours at 25° C., and the solvent was distilled off in vacuo. The residue was dissolved in water, the solution was extracted three times using dichloromethane, and the organic phase was dried (MgSO$_4$) and concentrated. Drying in vacuo gave 1.7 g (85%) of a white solid of melting point 98° C. to 100° C.

EXAMPLE 3

4-Benzyl-6-methyl-2-(5,6,7,8-tetrahydroquinolin-2-yl)-pyrimidine 2 ml of a 3-molar solution (0.006 mol) of methylmagnesium bromide in diethyl ether were added dropwise with vigorous stirring at 0° C. under an argon atmosphere to the suspension of 50 mg (0.00009 mol) of 1,3-bis-(diphenylphosphino)propanenickel(II) chloride and 1.0 g (0.003 mol) of 6-benzyl-4-chloro-2-(5,6,7,8-tetrahydroquinoin-2-yl-)-pyrimidine in 20 ml of absolute THF. The mixture was refluxed for 8 hours and subsequently stirred for 18 hours at room temperature. It was then poured into dilute hydrochloric acid, and the mixture was stirred for 30 minutes and neutralized using Na$_2$CO$_3$. The organic phase was dried and concentrated, and the residue was subjected to flash chromatography (silica gel, ethyl acetate). 0.4 g (42%) of a yellow oil were obtained. The compounds of Table 1 can be prepared analogously to these examples.

The hydrogen positions of the $^1$H NMR spectra are occupied as follows:

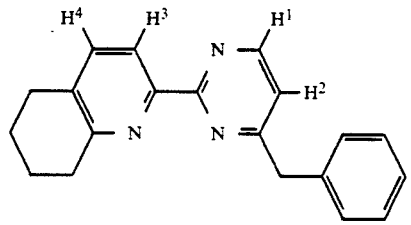

| Example No. | k | $R^1$ | $R^2$ | $R^3$ | $R^4$ | $R^5$ | $R^6$-$R^9$ | n | Physical data |
|---|---|---|---|---|---|---|---|---|---|
| 1.01 | 1 | H | H | H | H | H | H | 1 | m.p. = 90–91° C.; $^1$H NMR (CDCl$_3$) [ppm]: 8.74 (d), H$^1$; 8.23 (d), H$^4$; 7.55 (d), H$^3$; 7.34 (s, 5H); 6.97 (d), H$^2$ |
| 1.02 | 1 | H | H | CH$_3$ | H | H | H | 1 | m.p. = 57–60° C.; $^1$H NMR (CDCl$_3$) [ppm]: 8.20 (d), H$^4$; 7.50 (d), H$^1$; 7.31 (s, 5H); 6.95 (s), H$^2$ |
| 1.03 | 1 | H | Cl | H | H | H | H | 1 | $n_D^{30}$ = 1.6051 |
| 1.04 | 1 | H | H | CH$_3$ | CH$_3$ | H | H | 1 | m.p. = 121–123° C. |
| 1.05 | 1 | CH$_3$ | H | H | H | H | H | 1 | m.p. = 94–96° C. |
| 1.06 | 0 | H | H | H | H | H | H | 1 | |
| 1.07 | 0 | H | Cl | H | H | H | H | 1 | |
| 1.08 | 0 | H | H | H | H | H | 4-Cl | 1 | |
| 1.09 | 0 | H | H | H | H | H | 4-OCH$_3$ | 1 | |
| 1.10 | 0 | H | H | OCH$_3$ | H | H | H | 1 | |
| 1.11 | 0 | H | Cl | OCH$_3$ | CH$_3$ | H | H | 1 | |
| 1.12 | 1 | H | H | H | H | CH$_3$ | H | 1 | Fp. = 156–158° C.; $^1$H NMR (CDCl$_3$) [ppm]: 8.63 (d), H$^1$; 8.25 (d), H$^4$; 8.01–7.30 (m); 6.78 (d), H$^2$ |
| 1.13 | 1 | H | H | OCH$_3$ | H | H | 2,3 (—CH=CH—CH=CH—) | 1 | |
| 1.14 | 1 | H | Cl | OCH$_3$ | H | H | " | 1 | |
| 1.15 | 1 | CH$_3$ | H | H | H | H | (—CH$_2$—CH$_2$—CH$_2$—) | 1 | |
| 1.16 | 1 | CH$_3$ | Cl | H | H | H | (—CH$_2$—CH$_2$—CH$_2$—) | 1 | |
| 1.17 | 0 | H | H | CH$_2$—C$_6$H$_5$ | H | H | (—CH$_2$—CH$_2$—CH$_2$—) | 1 | |
| 1.18 | 0 | H | H | H | H | H | H | 1 | |
| 1.19 | 0 | H | Cl | H | H | H | 4-F | 1 | $n_D^{30}$ = 1.6025 |
| 1.20 | 0 | H | H | H | H | H | 4-F | 1 | m.p. = 101–102° C. |
| 1.21 | 0 | H | H | H | H | H | 2,4 Cl$_2$ | 1 | m.p. = 77–80° C. |
| 1.22 | 0 | H | Cl | H | H | H | 4-F | 1 | m.p. = 75–76° C. |
| 1.23 | 0 | H | H | H | H | H | 4-OCH$_3$ | 1 | $n_D^{30}$ = 1.6303 |
| 1.24 | 0 | H | Cl | H | H | H | 4-OCH$_3$ | 1 | m.p. = 80–81° C. |
| 1.25 | 0 | H | H | H | H | H | 4-Cl | 1 | $n_D^{30}$ = 1.6158 |
| 1.26 | 0 | H | Cl | H | H | H | 2,4-Cl$_2$ | 1 | |
| 1.27 | 0 | H | Cl | H | H | H | 2-Cl | 1 | |
| 1.28 | 0 | H | Cl | H | H | H | 4-F | 1 | |
| 1.29 | 0 | H | H | H | H | H | 4-CH$_3$ | 1 | |
| 1.30 | 0 | H | Cl | H | H | H | 2,4-Cl$_2$ | 1 | |
| 1.31 | 0 | H | H | H | H | H | 3-F | 1 | |
| 1.32 | 0 | H | H | H | H | H | 2,4-F$_2$ | 1 | |
| 1.33 | 0 | H | Cl | H | H | H | 2-F | 1 | |
| 1.34 | 0 | H | H | H | H | H | 3,4-F$_2$ | 1 | |
| 1.35 | 0 | H | Cl | H | H | H | 4-CH$_3$ | 1 | |
| 1.36 | 0 | H | H | H | H | H | 4-CF$_3$ | 1 | |
| 1.37 | 0 | H | Cl | H | H | H | 4-i-C$_4$H$_9$ | 1 | |
| 1.38 | 1 | H | H | H | H | H | 3-CF$_3$ | 1 | |
| 1.39 | 1 | H | Cl | H | H | H | 3-Cl | 1 | |
| 1.40 | 1 | H | Cl | H | H | H | 2-F, 4-Cl | 1 | |
| 1.41 | 1 | CH$_3$ | H | H | H | H | 3-CF$_3$ | 1 | |
| 1.42 | 1 | CH$_3$ | Cl | H | H | H | 4-CH$_3$ | 1 | |
| 1.43 | 1 | H | Cl | H | H | H | 4-Cl | 1 | |
| | | | | | | | 2-Cl | | |

-continued

| Example No. | k | R¹ | R² | R³ | R⁴ | R⁵ | R⁶–R⁹ | n | Physical data |
|---|---|---|---|---|---|---|---|---|---|
| 1.44 | 1 | H | Cl | H | H | H | 2-F | 1 | m.p. = 89–90° C. |
| 1.45 | 1 | H | Cl | H | H | H | 3-F | 1 | |
| 1.46 | 1 | H | H | H | H | H | 2-Cl | 1 | |
| 1.47 | 1 | H | H | H | H | H | 3-Cl | 1 | |
| 1.48 | 1 | H | H | H | H | H | 2,3-Cl₂ | 1 | |
| 1.49 | 1 | H | H | H | H | H | 2-F, 4-Cl | 1 | |
| 1.50 | 1 | H | H | H | H | H | 2-F | 1 | m.p. = 111–112° C. |
| 1.51 | 1 | H | H | H | H | H | 3-F | 1 | $n_D^{30}$ = 1.5985 |
| 1.52 | 1 | H | H | H | H | H | 3,4-F₂ | 1 | *HCl; m.p. = 200–201° C. |
| 1.53 | 1 | H | H | H | H | H | 3-CF₃ | 1 | m.p. = 134–135° C. |
| 1.54 | 1 | H | H | H | H | H | 4-CF₃ | 1 | |
| 1.55 | 1 | H | H | H | H | H | 4-CH₃ | 1 | m.p. = 82–83° C. |
| 1.56 | 1 | H | Cl | H | H | H | 4-t-C₄H₉ | 1 | |
| 1.57 | 1 | H | Cl | H | H | H | 3-Cl, 4-F | 1 | |
| 1.58 | 1 | H | Cl | H | H | H | 2-F, 4-CF₃ | 1 | |
| 1.59 | 2 | H | Cl | H | H | H | H | 1 | oil |
| 1.60 | 2 | H | Cl | H | H | H | 2,4-Cl₂ | 1 | $n_D^{30}$ = 1.6158; ¹H NMR (CDCl₃) [ppm]: 8.15 (d), H⁴: 7.47 (d), H³: 7.28 (s, 5H), 6.30 (s), H² |
| 1.61 | 2 | H | Cl | H | H | H | 4-F | 1 | oil; ¹H NMR (CDCl₃) [ppm]: 8.14 (d), H⁴: 7.47 (d), H³: 7.29 (s, 5H); 6.26 (s), H² |
| 1.62 | 2 | H | H | H | H | H | H | 1 | |
| 1.63 | 2 | H | H | H | H | H | 2,4-Cl₂ | 1 | |
| 1.64 | 2 | H | H | H | H | H | 4-F | 1 | |
| 1.65 | 2 | H | H | H | H | H | 4-Cl | 1 | |
| 1.66 | 2 | H | H | H | H | H | 3-Cl | 1 | |
| 1.67 | 2 | H | H | H | H | H | 3-CF₃ | 1 | |
| 1.68 | 2 | H | H | H | H | H | 4-CH₃ | 1 | |
| 2.01 | 1 | H | OCH₃ | H | H | H | H | 1 | |
| 2.02 | 1 | H | OC₂H₅ | H | H | H | H | 1 | |
| 2.03 | 1 | CH₃ | OCH₃ | H | H | H | 4-Cl | 1 | |
| 2.04 | 1 | CH₃ | O—C₄H₉ | H | H | H | 4-F | 1 | |
| 2.05 | 1 | H | OC₄H₉ | OCH₃ | H | H | 4-F | 1 | |
| 2.06 | 0 | H | OCH₃ | H | H | H | H | 1 | |
| 2.07 | 0 | H | OCH₃ | H | H | H | 2,4-Cl₂ (—CH₂—CH₂—CH₂—) | 1 | $n_D^{30}$ = 1.5945 |
| 2.08 | 0 | H | OC₂H₅ | H | H | H | 4-F | 1 | m.p. = 50–51° C.; ¹H NMR (CDCl₃) [ppm]: 8.15 (d), H⁴: 7.97–7.32 (m), 6.05 (s), H² |
| 2.09 | 1 | H | OCH₃ | H | H | H | (—CH=CH—CH=CH—) | 1 | |
| 2.10 | 1 | H | OCH₃ | H | H | H | H | 1 | |
| 2.11 | 1 | H | OC₂H₅ | H | H | H | 4-CF₃ | 1 | |
| 2.12 | 1 | H | OC₄H₉ | H | H | H | 3-CF₃ | 1 | |
| 2.13 | 1 | H | SCH₃ | H | H | H | (—CH=CH—CH=CH—) | 1 | |
| 2.14 | 1 | CH₃ | OCH₃ | H | H | H | (—CH₂—CH₂—CH₂—) | 1 | |
| 2.15 | 1 | CH₃ | OCH₃ | H | H | H | 4-Cl | 1 | |
| 2.16 | 1 | H | O—CH₂—C₆H₅ | H | H | H | H | 1 | |
| 2.17 | 1 | H | O—C₆H₅ | H | H | H | H | 1 | |
| 2.18 | 1 | H | O—CH₂—CH₂—OH | H | H | H | H | 1 | |
| 2.19 | 1 | H | O—CH₂—CH₂—OCH₃ | H | H | H | H | 1 | |
| 2.19 | 1 | H | O-Cyclohexyl | H | H | H | H | 1 | |
| 2.20 | 1 | H | O-Cyclopropyl | H | H | H | H | 1 | m.p. = 107–108° C. |

-continued

| Example No. | k | $R^1$ | $R^2$ | $R^3$ | $R^4$ | $R^5$ | $R^6$–$R^9$ | n | Physical data |
|---|---|---|---|---|---|---|---|---|---|
| 2.21 | 1 | H | OCH$_3$ | H | H | H | 4-F | 1 | $n_D^{30}$ = 1.6050 |
| 2.22 | 1 | H | OCH$_3$ | H | H | H | 4-Cl | 1 | m.p. = 138–139° C. |
| 2.23 | 1 | H | OCH$_3$ | H | H | H | 2,4-Cl$_2$ | 1 | |
| 2.24 | 0 | H | OCH$_3$ | H | H | H | 4-OCH$_3$ | 1 | |
| 2.25 | 1 | H | O—CH$_2$—CH$_2$—OH | H | H | H | 4-F | 1 | |
| 2.26 | 1 | H | OCF$_3$ | H | H | H | 4-Cl | 1 | |
| 2.27 | 1 | H | CH$_3$ | H | H | H | H | 1 | |
| 2.28 | 1 | H | C$_6$H$_5$ | H | H | H | H | 1 | m.p. = 38–39° C.; $^1$H NMR (CDCl$_3$) [ppm]: 8.15 (d), H4; 8.00–7.29 (m); 6.04 (s), H2 |
| 2.29 | 0 | H | S—C$_6$H$_5$ | H | H | H | (—CH=CH—CH=CH—) | 1 | |
| 2.30 | 1 | H | OC$_2$H$_5$ | H | H | H | (—CH=CH—CH=CH—) | 1 | m.p. = 98–100° C.; $^1$H NMR (CDCl$_3$) [ppm]: 8.11 (d), H4; 7.53–7.13 (m); 6.14 (s), H2 |
| 2.31 | 1 | H | OC$_2$H$_5$ | H | H | H | 2,4-Cl$_2$ | 1 | $n_D^{30}$ = 1.5915 |
| 2.32 | 1 | H | OC$_2$H$_5$ | H | H | H | 2,4-Cl$_2$ | 1 | |
| 2.33 | 1 | H | O—C$_4$H$_9$ | H | H | H | 4-Cl | 1 | |
| 2.34 | 0 | H | C$_6$H$_5$ | H | H | H | (—CH=CH—CH=CH—) | 1 | |
| 2.35 | 0 | H | O—C$_6$H$_5$ | H | H | H | 4-Cl | 1 | |
| 2.36 | 1 | CH$_3$ | O—CH$_2$—CH=CH$_2$ | H | H | H | 4-Cl | 1 | |
| 2.37 | 1 | H | O—CH$_2$—CH=CH$_2$ | CH$_3$ | H | H | 4-Cl | 1 | m.p. = 93–94° C. |
| 2.38 | 1 | H | O—CH$_2$—CH=CH$_2$ | H | H | H | (—CH$_2$—CH$_2$—CH$_2$—) | 1 | |
| 2.39 | 1 | H | O—CH$_2$—C≡CH | H | H | H | 4-Cl | 1 | |
| 2.40 | 0 | H | O—CH$_2$—C≡CH | H | H | H | 4-Cl | 1 | |
| 2.41 | 1 | H | O—CH$_2$—C≡CH | H | H | H | (—CH=CH—CH=CH—) | 1 | |
| 2.42 | 1 | H | O—CH$_2$—C≡CH | H | H | H | 2,4-Cl$_2$ | 1 | |
| 2.43 | 1 | H | O—C$_8$H$_{17}$ | H | H | H | 4-F | 1 | |
| 2.44 | 1 | H | O—C$_{18}$H$_{37}$ | H | H | H | H | 1 | $n_D^{30}$ = 1.6141 |
| 2.45 | 1 | H | CH$_2$—CH$_3$ | H | H | H | 4-F | 1 | |
| 2.46 | 1 | H | OCF$_3$ | H | H | H | H | 1 | |
| 2.47 | 0 | H | O—CF$_2$—CF$_3$ | H | H | H | H | 1 | |
| 2.48 | 1 | H | OCF$_3$ | H | H | H | 4-CH$_3$ | 1 | |
| 2.49 | 1 | H | OCH$_3$ | H | H | H | 4-CH$_3$ | 1 | |
| 2.50 | 1 | H | SCH$_3$ | H | H | H | 4-CH$_3$ | 1 | |
| 2.51 | 1 | H | OC$_4$H$_9$ | H | H | H | 4-CH$_3$ | 1 | |
| 2.52 | 1 | H | OCHF$_2$ | H | H | H | 4-CH$_3$ | 1 | |
| 2.53 | 1 | H | OCH$_3$ | H | H | H | 3,4-F$_2$ | 1 | |
| 2.54 | 1 | H | OC$_2$H$_5$ | H | H | H | 3,4-F$_2$ | 1 | |
| 2.55 | 1 | H | SCH$_3$ | H | H | H | 3,4-F$_2$ | 1 | |
| 2.56 | 1 | H | OC$_4$H$_9$ | H | H | H | 2,4-F$_2$ | 1 | |
| 2.57 | 1 | H | OC$_3$H$_7$ | H | H | H | 2,4-F$_2$ | 1 | |
| 2.58 | 1 | H | OCH$_3$ | H | H | H | 2-F, 4-C$_4$H$_9$ | 1 | |
| 2.59 | 1 | H | OCH$_3$ | H | H | H | 4-t-C$_4$H$_9$ | 1 | |
| 2.60 | 1 | H | OC$_2$H$_5$ | H | H | H | 4-t-C$_4$H$_9$ | 1 | |
| 2.61 | 1 | H | SC$_2$H$_5$ | H | H | H | 4-t-C$_4$H$_9$ | 1 | |
| 2.62 | 1 | H | OCH$_2$CH$_2$OH | H | H | H | 4-F | 1 | m.p. = 117–119° C. |
| 2.63 | 1 | H | OCH$_2$—C≡CH | H | H | H | 4-OCH$_3$ | 1 | $n_D^{30}$ = 1.5752 |
| 2.64 | 1 | H | OCH$_2$CF$_3$ | H | H | H | 4-OCH$_3$ | 1 | $n_D^{30}$ = 1.5710 |
| 2.65 | 1 | H | OCH(CF$_3$)$_2$ | H | H | H | 4-OCH$_3$ | 1 | m.p. = 186–188° C. |
| 2.66 | 1 | H | OCHF$_2$ | H | H | H | 4-OCH$_3$ | 1 | $n_D^{30}$ = 1.5958 |
| 2.67 | 1 | H | OCH$_2$CH(OH)CH$_2$OH | H | H | H | 4-OCH$_3$ | 1 | m.p. = 120–121° C. |
| 2.68 | 1 | H | OCH$_2$CH(OH)CH$_2$OH | H | H | H | H | 1 | |

-continued

| Example No. | k | $R^1$ | $R^2$ | $R^3$ | $R^4$ | $R^5$ | $R^6$–$R^9$ | n | Physical data |
|---|---|---|---|---|---|---|---|---|---|
| 3.01 | 1 | H | O—CH$_2$—C≡CH | H | H | H | H | 1 | oil; $^1$H NMR (CDCl$_3$) [ppm]: 8.17 (d), H$^4$, 7.43 (d), H$^3$; 7.27 (s, 5H); 6.36 (s) H$^2$ |
| 3.02 | 1 | H | SCH$_3$ | H | H | H | H | 1 | oil; $^1$H NMR (CDCl$_3$) [ppm]: 8.15 (d), H$^4$, 7.48 (d), H$^3$; 7.30 (s, 5H); 6.75 (s), H$^2$ |
| 3.03 | 1 | H | Cl | H | H | H | (—CH=CH—CH=CH—) | 1 | m.p. = 149–150° C.; $^1$H NMR (CDCl$_3$) [ppm]: 8.20 (d), H$^4$, 8.00–7.30 (m); 6.75 (s), H$^2$ |
| 3.04 | 1 | H | Cl | H | H | H | 2,4,6-Cl$_3$ | 1 | |
| 3.05 | 1 | H | O—CH$_2$—C$_6$H$_4$—Cl | H | H | H | 4-Cl | 1 | |
| 3.06 | 1 | H | Cl | H | H | H | 2,4-Cl$_2$ | 1 | oil; $^1$H NMR (CDCl$_3$) [ppm]: 8.15 (d), H$^3$; 7.57–7.10 (m); 6.93 (s), H$^2$ |
| 3.07 | 0 | H | Cl | H | H | H | 4-Cl | 1 | oil |
| 3.08 | 1 | H | Cl | H | H | H | 4-Cl | 1 | oil; $^1$H NMR (CDCl$_3$) [ppm]: 8.18 (d), H$^4$, 7.50 (d), H$^3$; 7.27 (m); 6.96 (s), H$^2$ |
| 3.09 | 1 | H | OH | H | H | H | (—CH=CH—CH=CH—) | 1 | m.p. = 152–154° C.; $^1$H NMR (CDCl$_3$) [ppm]: 8.12 (d), H$^4$, 8.00–7.30 (m); 5.95 (s), H$^2$ |
| 3.10 | 0 | H | OCH$_2$—CH$_2$—OH | H | H | H | H | 1 | |
| 3.11 | 0 | H | OCH$_2$—CH$_2$—OH | (—CH$_2$—CH$_2$—CH$_2$—) | H | H | H | 1 | |
| 3.12 | 1 | H | OCH$_2$—CH$_2$—OH | (—CH$_2$—CH$_2$—CH$_2$—) | H | H | H | 1 | |
| 3.13 | 1 | H | OC$_2$H$_5$ | H | H | H | 4-Cl | 1 | m.p. = 86–87° C. |
| 3.14 | 1 | H | O—C$_4$H$_9$ | H | H | H | H | 1 | $n_D^{30}$ = 1.5855 |
| 3.15 | 1 | H | OCH$_3$ | H | H | H | 3-(O—C$_6$H$_5$) | 1 | |
| 3.16 | 1 | H | OCH$_3$ | H | H | H | 4-(O—C$_6$H$_5$) | 1 | |
| 3.17 | 0 | H | Cl | H | H | H | (—CH$_2$—CH$_2$—CH$_2$—CH$_2$—) | 1 | |
| 3.18 | 2 | H | OCH$_3$ | H | H | H | H | 1 | $n_D^{30}$ = 1.5985 |
| 3.19 | 2 | H | OC$_2$H$_5$ | H | H | H | H | 1 | $n_D^{30}$ = 1.6015 |
| 3.20 | 2 | H | OCH$_3$ | H | H | H | 2,3-F$_2$ | 1 | |
| 3.21 | 2 | H | SCH$_3$ | H | H | H | 2,3-F$_2$ | 1 | |
| 3.22 | 2 | H | SO$_2$H$_5$ | H | H | H | 2,3-F$_2$ | 1 | |
| 3.23 | 2 | H | OCH$_3$ | H | H | H | 2,4-Cl$_2$ | 1 | $n_D^{30}$ = 1.5945 |
| 3.24 | 2 | H | OCH$_3$ | H | H | H | 3,4-Cl$_2$ | 1 | |
| 3.25 | 2 | H | OC$_2$H$_5$ | H | H | H | 3-Cl | 1 | |
| 3.26 | 2 | H | OCH$_3$ | H | H | H | 4-Cl | 1 | $n_D^{30}$ = 1.5930 |
| 3.27 | 0 | H | OC$_2$H$_5$ | H | H | H | H | 1 | $n_D^{30}$ = 1.6012 |
| 3.28 | 0 | H | OCH$_3$ | H | CH$_3$ | H | H | 1 | |

C. BIOLOGICAL EXAMPLES

EXAMPLE 1

Rice plants cv. "Ballila", approx. 5 weeks old, were treated with the claimed compounds in the concentrations mentioned below. After the spray coating had dried on, the plants were inoculated uniformly with a spore suspension of Pyricularia oryzae and placed in a controlled-environment cabinet in darkness at a temperature of 25° C. and 100% relative atmospheric humidity for 48 h. The rice plants were then grown on in a greenhouse at a temperature of 25° C. and a relative atmospheric humidity of 80%. The level of disease was scored after 5 days. The disease level was expressed in % diseased leaf area compared with untreated, infected control plants. The results are compiled in Table 1.

TABLE 1

| Compound according to Example | Leaf area diseased with Pyricularia oryzae in % at mg of active substance/ liter of spray liquor |
|---|---|
| 1.01 | 0 |
| 2.01 | 0 |
| 1.20 | 0 |
| 1.21 | 0 |
| 2.67 | 0 |
| 1.05 | 0 |
| 1.24 | 0 |
| 1.62 | 0 |
| untreated, infected plants | 100 |

EXAMPLE 2

Field beans cv. "Herz Freya" or "Frank's Ackerperle", approx. 14 days old, were treated to runoff point with aqueous suspensions of the claimed compound.

After the spray coating had dried on, the plants were inoculated with a spore suspension (1.5 million spores/ml) of Botrytis cinerea. The plants were grown on in a controlled-environment cabinet at 20°-22° C. and approx. 99% relative atmospheric humidity. The infection of the plants manifested itself in the formation of black spots on leaves and stalks. The tests were evaluated approximately approx. 1 week after inoculation.

The disease level is expressed in % diseased leaf area, compared with untreated, infected control plants (=100%). The result can be seen from Table 2.

TABLE 2

| Compound according to Example | Leaf area diseased with Botrytis cinerea in % at mg of active substance/ liter of spray liquor | | |
|---|---|---|---|
| | 500 | 250 | 125 |
| 1.03 | 0 | 0 | — |
| 1.01 | 0 | 0 | 0 |
| 3.02 | 0 | 10 | 10 |
| 2.01 | 0 | 0 | 0 |
| 2.02 | 0 | 10 | — |
| 2.64 | — | 0 | — |
| 1.20 | — | 0 | — |
| 1.19 | — | 0 | — |
| 1.21 | — | 0 | — |
| 2.09 | — | 0 | — |
| 1.23 | — | 0 | — |
| 2.68 | — | 0 | — |
| 2.67 | — | 0 | — |
| 1.05 | — | 0 | — |
| 1.24 | — | 0 | — |
| 1.46 | — | 0 | — |
| 1.62 | — | 0 | — |
| 3.26 | — | 0 | — |
| untreated infected plants | | 100 | |

EXAMPLE 3

Wheat plants cv. "Jubilar" in the 2-leaf stage were treated to runoff point with aqueous suspensions of the preparations given in Table 2.

After the spray coating had dried, the plants were inoculated with an aqueous pyknospore suspension of Leptosphaeria nodorum and incubated in a controlled-environment cabinet for several hours at 100% relative atmospheric humidity. The plants were grown on in the greenhouse at approx. 90% relative atmospheric humidity until the symptoms became manifest.

The disease level was expressed in % diseased leaf surface compared with untreated, infected control plants and can be seen from Table 3.

TABLE 3

| Compound according to Example | Leaf area diseased with Leptosphaeria nodorum in % at mg of active substance/ liter of spray liquor | | |
|---|---|---|---|
| | 500 | 250 | 125 |
| 1.03 | 0 | 0 | 0 |
| 1.01 | 0 | 0 | 0 |
| 3.02 | 0 | 0 | 0 |
| 2.01 | 0 | 0 | — |
| 2.02 | 0 | 0 | 0 |
| 3.08 | — | 0 | — |
| 1.19 | — | 0 | — |
| 1.21 | — | 0 | — |
| 2.09 | — | 0 | — |
| 1.23 | — | 0 | — |
| 2.68 | — | 0 | — |
| 2.65 | — | 0 | — |
| 2.67 | — | 0 | — |
| 1.05 | — | 0 | — |
| 1.24 | — | 0 | — |
| 3.18 | — | 0 | — |
| 1.59 | — | 0 | — |
| untreated infected plants | | 100 | |

EXAMPLE 4

Barley plants cv. "Igri" in the 2-leaf stage were treated to runoff point with an aqueous suspension of the claimed compounds.

After the spray coating had dried on, the plants were inoculated with an aqueous spore suspension of Pyrenophora teres and incubated for 16 hours in a controlled-environment cabinet at 100% relative atmospheric humidity. The infected plants were then further grown in the greenhouse at 25° C. and 80% relative atmospheric humidity.

The disease was evaluated approx. 1 week after inoculation. The disease level was scored as a % of diseased leaf area compared with the untreated, infected control, and can be seen from Table 4.

TABLE 4

| Compound according to Example | Leaf area diseased with Pyrenophora teres in % at mg of active substance/liter of spray liquor | | |
|---|---|---|---|
| | 500 | 250 | 125 |
| 1.03 | 0 | 0 | 0 |
| 1.01 | 0 | 0 | 0 |
| 2.02 | 0 | 0 | 0 |
| 2.64 | — | 0 | — |
| 2.22 | — | 0 | — |
| 1.19 | — | 0 | — |
| 1.21 | — | 0 | — |
| 2.09 | — | 0 | — |
| 1.20 | — | 0 | — |
| 2.63 | — | 0 | — |
| 2.17 | — | 0 | — |
| 1.23 | — | 0 | — |
| 2.68 | — | 0 | — |
| 2.67 | — | 0 | — |
| 1.05 | — | 0 | — |
| 1.24 | — | 0 | — |
| 1.62 | — | 0 | — |
| 3.18 | — | 0 | — |
| 3.26 | — | 0 | — |
| untreated, infected plants | | 100 | |

We claim:

1. A pyrimidine derivative of the formula I

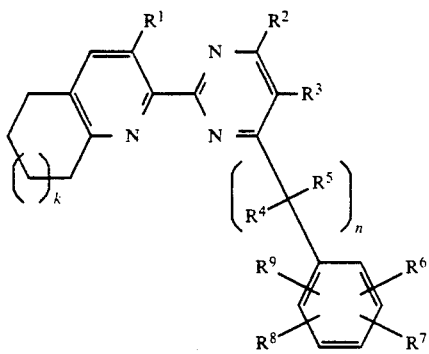

in which $R^1$ is hydrogen, $(C_1-C_6)$alkyl, $(C_1-C_6)$alkoxy, phenyl$(C_1-C_4)$alkyl, it being possible for the phenyl moiety to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, $R^2$ is hydrogen, hydroxyl, $(C_2-C_4)$alkenyl-$(C_1-C_4)$alkyl, $(C_2-C_4)$alkynyl-$(C_1-C_4)$alkyl, $(C_1-C_6)$alkyl, $(C_1-C_4)$alkoxy-$(C_1-C_4)$alkyl, $(C_2-C_6)$alkenyl, $(C_2-C_6)$alkynyl, $(C_3-C_7)$cycloalkyl, $(C_3-C_7)$cycloalkyl-$(C_1-C_4)$alkyl, it being possible for the two last-mentioned radicals to be up to trisubstituted in the cycloalkyl moiety by $(C_1-C_4)$alkyl, or is phenyl, phenoxy-$(C_1-C_4)$alkyl, phenyl-$(C_1-C_4)$alkyl, it being possible for the three last-mentioned radicals to be up to trisubstituted in the phenyl moiety by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, or is $(C_1-C_{12})$alkoxy, $(C_2-C_6)$alkenyl-$(C_1-C_4)$alkoxy, $(C_2-C_6)$alkynyl-$(C_1-C_4)$alkoxy, $(C_3-C_7)$cycloalkoxy, $(C_1-C_6)$alkoxy-$(C_1-C_6)$alkoxy, hydroxy-$(C_1-C_6)$alkoxy, $(C_1-C_6)$haloalkoxy, $(C_1-C_6)$alkylthio, $(C_2-C_6)$alkenyl-$(C_1-C_4)$alkylthio, $(C_2-C_6)$-alkynyl-$(C_1-C_4)$alkylthio, $(C_3-C_7)$cycloalkylthio, phenoxy, phenylthio, phenyl-$(C_1-C_6)$alkoxy, phenyl$(C_1-C_6)$alkylthio, phenyl-$(C_1-C_2)$alkoxy-$(C_1-C_4)$alkoxy, it being possible for the phenyl ring in the five last-mentioned radicals to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy or monosubstituted by nitro or cyano, $R^3$ is hydrogen, $(C_1-C_6)$alkyl, $(C_1-C_4)$haloalkyl, $(C_1-C_4)$alkoxy, $(C_1-C_4)$alkylthio, halogen, phenyl, phenyl$(C_1-C_4)$alkyl, it being possible for the phenyl radical of the three last-mentioned radicals to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy or monosubstituted by nitro or cyano, $R^4$ and $R^5$ independently of one another are hydrogen $(C_1-C_5)$alkyl, or $R^3$ together with $R^4$ or $R^5$ is a component of a maximally unsaturated $\gamma$-membered ring where $\gamma = 3$ to 8, $R^6$, $R^7$, $R^8$ and $R^9$ independently of one another are hydrogen, halogen, nitro, cyano, $(C_1-C_6)$alkyl, $(C_1-C_6)$alkoxy, $(C_1-C_6)$alkylthio, $(C_1-C_6)$haloalkyl, $C_1-C_6$ haloalkoxy, phenyl, phenoxy, it being possible for the two last-mentioned radicals to be up to trisubstituted in the phenyl radical by halogen, $(C_1-C_4)$alkyl, $(C_1-C_4)$alkoxy, $(C_1-C_4)$haloalkyl or $(C_1-C_4)$haloalkoxy, two of the radicals $R^6$ to $R^9$ may form a component of an unsaturated or saturated m-membered ring where m is 5 or 6, k is 0, 1 or 2, n is 1 or 2 and halo has the meaning of monosubstituted or polysubstituted by halogen atoms, and the acid addition salts thereof.

2. A compound of the formula I as claimed in claim 1, in which $R^1$ is hydrogen, $(C_1-C_4)$alkyl, $(C_1-C_5)$alkoxy, $R^2$ is hydrogen, hydroxyl, $(C_1-C_4)$alkyl, $(C_2-C_4)$alkenyl$(C_1-C_2)$alkyl, $(C_2-C_4)$alkynyl-$(C_1-C_2)$alkyl, $(C_1-C_4)$alkoxy-$(C_1-C_4)$alkyl, $(C_2-C_4)$alkenyl, $(C_2-C_4)$alkynyl, $(C_3-C_6)$cycloalkyl, $(C_3-C_6)$cycloalkyl-$(C_1-C_2)$alkyl, it being possible for the two last-mentioned radicals to be up to trisubstituted in the cycloalkyl moiety by $(C_1-C_4)$alkyl, or is phenyl, phenoxy-$(C_1-C_2)$alkyl, phenyl$(C_1-C_2)$alkyl, it being possible for the three last-mentioned radicals to be up to trisubstituted in the phenyl moiety by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, or is $(C_1-C_{12})$alkoxy, $(C_2-C_4)$alkenyl-$(C_1-C_2)$alkoxy, $(C_2-C_4)$alkynyl-$(C_1-C_2)$alkoxy, $(C_3-C_6)$cycloalkyloxy, $(C_1-C_4)$alkoxy-$(C_1-C_4)$alkoxy, hydroxy-$(C_1-C_4)$alkoxy, $(C_1-C_6)$haloalkoxy, $(C_1-C_6)$alkylthio, $(C_2-C_6)$alkenyl-$(C_1-C_2)$alkylthio, $(C_2-C_4)$alkynyl-$(C_1-C_2)$alkylthio, $(C_3-C_6)$cycloalkylthio, phenoxy, phenylthio, phenyl-$(C_1-C_2)$alkoxy, phenyl$(C_1-C_2)$alkylthio, phenyl-$(C_1-C_2)$alkoxy-$(C_1-C_4)$alkoxy, it being possible for the phenyl ring in the four last-mentioned radicals to be up to trisubstituted by halogen, $(C_1-C_4)$alkyl, $(C_1-C_4)$alkoxy, $(C_1-C_4)$alkylthio, $(C_1-C_4)$haloalkyl or $(C_1-C_4)$haloalkoxy, $R^3$ is hydrogen, $(C_1-C_4)$alkyl, $(C_1-C_4)$haloalkyl, $(C_1-C_4)$alkoxy, $(C_1-C_4)$alkylthio, halogen, phenyl, phenyl-$(C_1-C_2)$alkyl, $R^4$ and $R^5$ independently of one another are hydrogen or $(C_1-C_2)$alkyl or $R^3$ together with $R^4$ or $R^5$ is a component of a maximally unsaturated $\gamma$-membered ring where $\gamma$ is 5 or 6, $R^6$, $R^7$, $R^8$ and $R^9$ independently of one another are hydrogen, halogen, nitro, cyano, $(C_1-C_4)$alkyl, $(C_1-C_4)$alkoxy, $(C_1-C_4)$haloalkyl, $(C_1-C_4)$haloalkoxy, phenyl, phenyloxy, it being possible for the two last-mentioned radicals to be up to trisubstituted in the phenyl radical by halogen, $(C_1-C_4)$alkyl, $(C_1-C_4)$alkoxy, $(C_1-C_4)$haloalkyl or $(C_1-C_4)$haloalkoxy, two of the radicals $R^6$ to $R^9$ may form a component of an unsaturated or saturated m-membered ring where m is 5 or 6, k is 0, 1 or 2, n is 1 or 2 and halo has the meaning of monosubstituted of polysubstituted by halogen atoms, and the acid addition salts thereof.

3. Fungicidal composition, which contains an effective amount of a compound of the formula I as claimed in claim 1 and a carrier.

4. A method of controlling harmful fungi, which comprises applying an effective amount of a compound of the formula I as claimed in claim 1 to these harmful fungi or the plants, surfaces or substrates infected with them.

* * * * *